United States Patent
DeLuisa et al.

(10) Patent No.: US 6,623,517 B1
(45) Date of Patent: *Sep. 23, 2003

(54) EYE COMPRESS

(76) Inventors: Laura DeLuisa, 12122 Ostsego St., Valley Village, CA (US) 91607; Cristina Bartolucci, 2344 Griffith Park Blvd., Los Angeles, CA (US) 90039

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/507,864

(22) Filed: Feb. 22, 2000

Related U.S. Application Data
(60) Provisional application No. 60/121,295, filed on Feb. 23, 1999.

(51) Int. Cl.$^7$ .................................................. A61F 7/00
(52) U.S. Cl. ...................... 607/109; 607/104; 604/294; 165/46
(58) Field of Search .................................. 607/104, 109; 165/46, 73; 2/9; 604/294, 295, 303; 128/112.1–115.1

(56) References Cited

U.S. PATENT DOCUMENTS

| | | | |
|---|---|---|---|
| 3,762,419 A | * 10/1973 | Walters ...................... 128/403 |
| 3,768,485 A | * 10/1973 | Linick ......................... 128/402 |
| 3,868,984 A | * 3/1975 | Jorgensen ................... 150/2.3 |
| 4,243,041 A | * 1/1981 | Paul ............................ 128/402 |
| 4,372,318 A | * 2/1983 | Viesturs et al. ............. 128/403 |
| 4,700,706 A | * 10/1987 | Munch ......................... 128/403 |
| 4,979,811 A | * 12/1990 | Boyer .......................... 351/44 |
| 5,124,313 A | * 6/1992 | Schaeffer et al. ............. 514/2 |
| 5,980,904 A | * 11/1999 | Leverett et al. ........... 424/195.1 |
| 6,159,487 A | * 12/2000 | Znaiden et al. .............. 424/402 |
| 6,193,740 B1 | * 2/2001 | Rodriguez ............. 606/204.25 |
| 6,241,711 B1 | * 6/2001 | Weissberg et al. ........... 604/291 |
| 6,254,896 B1 | * 7/2001 | Davis .......................... 424/725 |

FOREIGN PATENT DOCUMENTS

| | | | |
|---|---|---|---|
| DE | 3411357 A1 | * 10/1985 | ............ A61F/7/08 |
| EP | 0945136 A1 | * 9/1999 | |
| WO | 99/32047 | * 1/1999 | |

OTHER PUBLICATIONS

Pond's "Soothing Cucumber Eye Treatments." Appendix A.*

* cited by examiner

Primary Examiner—Linda C. M. Dvorak
Assistant Examiner—A. Farah
(74) Attorney, Agent, or Firm—Garrettson Ellis; Seyfarth Shaw

(57) ABSTRACT

A cooled, therapeutic gelatinous disc is provided which includes a convex face configured to overlie a typical human eye and a surrounding margin of tissue. The convex face of the disc includes a non-planar surface, which presents a non-uniform, three-dimensional surface for contacting the eye. Water, gelatin powder, therapeutic plant extracts and oils, methylparaben, diazolidinyl urea and a coloring agent are mixed, poured into a mold and then cooled to form a cooled gelatinous disc having a convex face with the raised swirl design. A plastic film is attached to the mold to hermetically seal the gelatinous disc, which sealed assembly is stored in a light-impermeable and resealable bag. The gelatinous disc may be removed from the mold and placed onto the eye and surrounding tissue, preferably in connection with a moisturizer, in order to relieve irritation.

26 Claims, 2 Drawing Sheets

EYE COMPRESS

RELATED APPLICATION

This application claims priority from provisional application Serial No. 60/121,295 filed Feb. 23, 1999.

BACKGROUND OF THE INVENTION

This invention relates generally to eye compresses. More particularly, the present invention relates to a gelatin based elongated disc having therapeutic plant extracts which forms a disposable eye compress for relieving eye irritation.

Eye compresses employing either liquid soaked gauze pads or gel filled polyurethane "masks" for relieving swelling and providing general comfort to the eye area are well known and commercially available. Existing eye compresses either wet the eyelid with an odorless topical solution or distribute coolness to the eyebrow and cheek bone area.

Although the use of eye compresses to relieve irritated eye tissue is not new, the compresses themselves have traditionally been less than ideal. The placement of a gel filled mask over the eyes deprives the eyelid area of coolness. Although liquid soaked pads target the eyelid area, the pads warm almost immediately upon contact with the skin. Further, existing eye compresses do not employ the benefits of aroma therapy.

Accordingly, there has been a need for a novel eye compress which is comprised of a gelatinous material that can be manufactured in an economical fashion and include therapeutic substances. Such a novel eye compress is needed which may employ the benefits of aroma therapy, and is specifically designed to conform to the shape of the eye and adhere to it. Additionally, what is needed is an eye compress which is packaged so as to be easily used while retaining the benefits of its composition. The present invention fulfills these needs and provides other related advantages.

SUMMARY OF THE INVENTION

The present invention resides in a novel eye compress generally comprised of a cooled, gelatinous disk, free of cloth pads, having a convex face configured to overlie a typical human eye and surrounding margin of tissue so that therapeutic plant extracts and oils within the gelatinous disk can relieve and reduce irritation of the eye and surrounding tissue. The gelatinous disk is specifically comprised of a mixture of deionized water, 300 blum gelatin powder, therapeutic plant extracts, peg 40 hydrogenated castor oil, methylparaben, diazolidinyl, urea, a coloring agent, and aromatherapeutic oils.

The convex face of the disc includes a non-planar surface which presents a non-uniform, three-dimensional surface for contacting the eye. Preferably, this non-planar surface includes a swirl pattern. The gelatinous disc is housed in a rigid mold which corresponds to the shape of the gelatinous disc. The mold includes a plastic film removably covering an open face of the mold so as to hermetically seal the gelatinous disc within the mold. The mold containing the gelatinous disc is typically stored in a light-impermeable and resealable bag.

To make the eye compress, the hot deionized water, gelatin powder, therapeutic plant extracts, hydrogenated castor oil, methylparaben, diazolidinyl urea, coloring agent and aromatherapeutic oils are mixed to create a gelatinous mixture. The gelatinous mixture is then poured into the mold and cooled to form a cooled gelatinous disc having a convex face with a raised swirl design. The plastic film is attached to the mold to hermetically seal the gelatinous disc. The hermetically sealed mold housing the gelatinous disc eye compress is stored in the light-impermeable and resealable bag until use.

In use, a moisturizer is applied either to an eyelid and surrounding tissue area, or preferably to the convex face of the gelatinous disc itself. After removing the gelatinous disc from the mold, it is placed convex face down onto the eye and surrounding tissue in order to distribute coolness directly to the eye lid and under eye, area where puffiness occurs. This covered facial tissue is then allowed to absorb the benefits of the various therapeutic plant extracts and oils to further relieve irritation.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
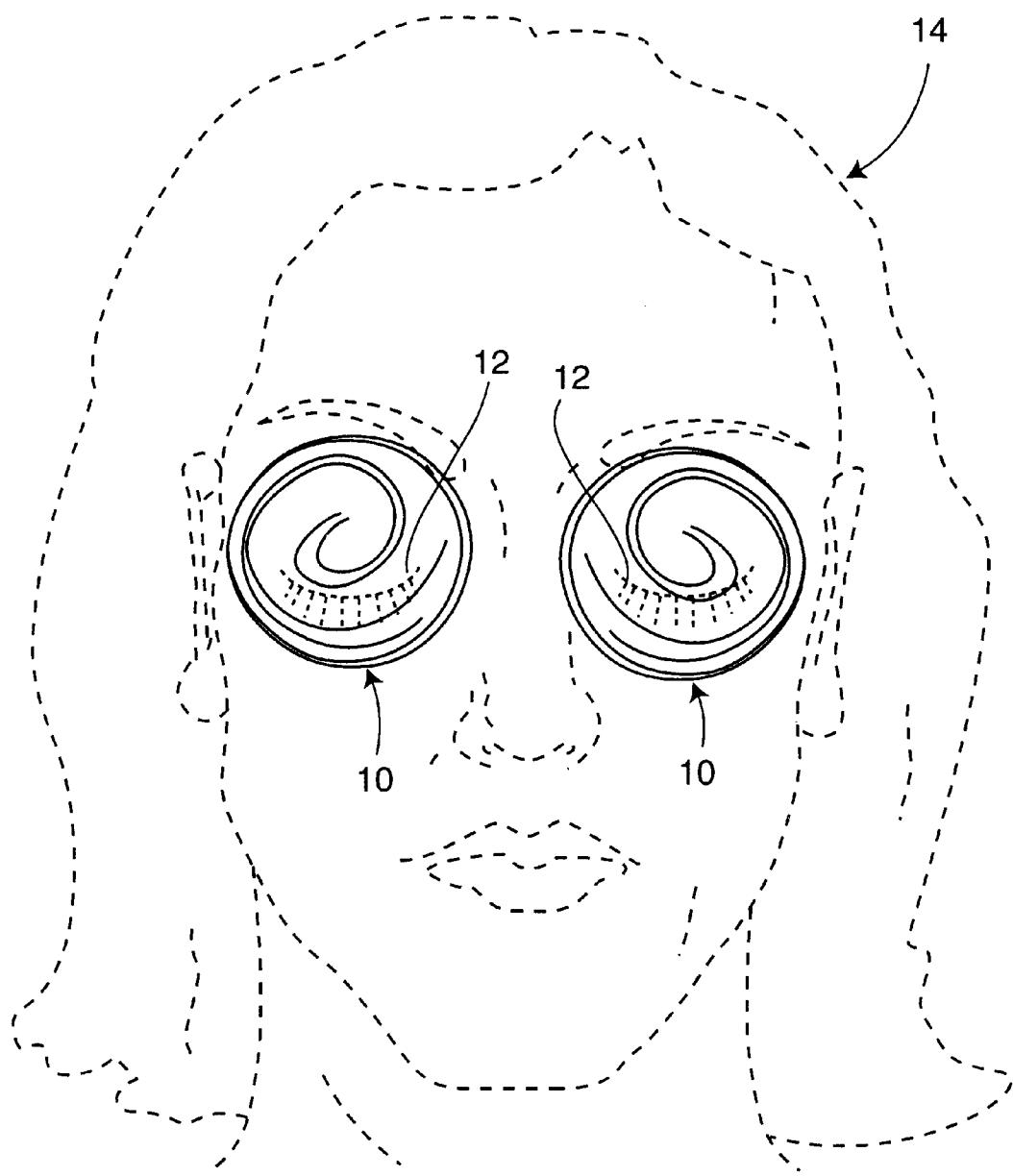
FIG. 1 is an environmental view of eye compresses embodying the present invention placed over the eyes and surrounding tissue of a user's face.

As shown in the drawings for purposes of illustration, the present invention relates to an eye compress 10 which is positionable over the eye 12 and surrounding area while a user 14 is in a reclined position in order to reduce and relieve eye and surrounding tissue irritation (see FIG. 1). Typically, the eye compress 10 is packaged and utilized in pairs.

The eye compress 10 is comprised of a gelatinous disc 16 having a convex face 18 which is configured to overlie the user's eye 12, the surrounding eyelid, and lower eye area, where puffiness and irritation commonly occur. The disc 10 is somewhat elongated, being approximately 2.25 inches in width by 2.875 inches in length, and is approximately 0.125 inch in thickness, although it is not restricted to such dimensions. The gelatinous disc 10 is typically of a translucent color.

The eye compress 10 is made by mixing hot deionized water, 300 blum gelatin powder, plant extracts, peg 40 hydrogenated castor oil, methylparaben, diazolidinyl urea, a coloring agent such as FD&C blue #1, and aromatherapeutic oils. The plant extracts can include plant collagen, comfrey extracts, vitamin C and arnica extracts. The aromatherapeutic oils can include lavender, tangerine, wisteria, grapefruit. The gelatinous mixture is poured into a specially designed mold 20 and chilled at 40° F. until set, which typically takes about one half hour.

Figure 2:
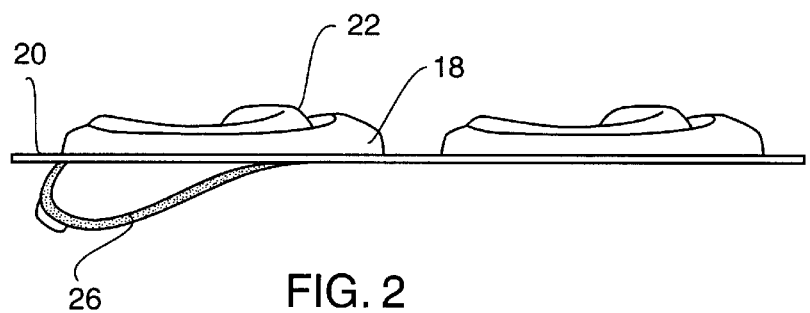
FIG. 2 is an elevational view of a mold containing the eye compresses of FIG. 1, further illustrating the removal of a plastic film from the mold to access the eye compresses.
Figure 3:
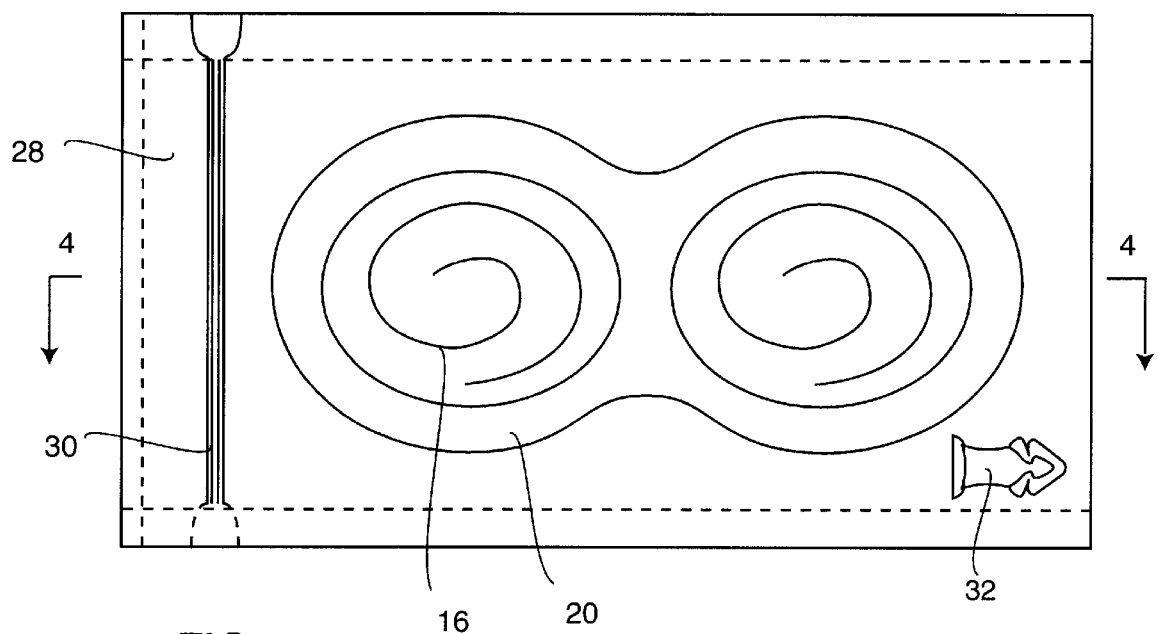
FIG. 3 is a top plan view of a resealable bag containing the mold housing the eye compresses of FIG. 2, and a moisturizer packet.
Figure 4:
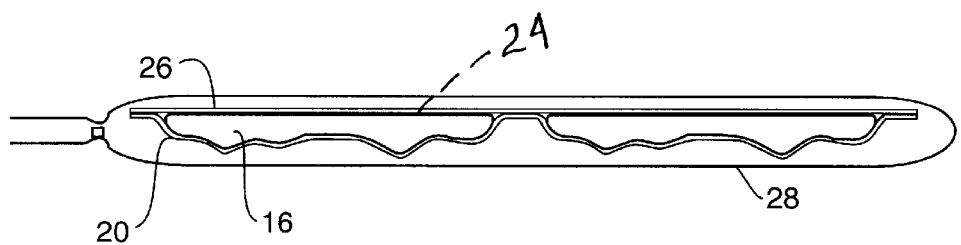
FIG. 4 is a cross-sectional view taken generally along line 4—4 of FIG. 3, illustrating the convex and irregular shape of the mold and eye compresses.

Referring to FIGS. 2 through 4, the mold 20 is preferably comprised of a rigid clear plastic material, such as polyurethane, and configured to impart the convex face 18 and a non-planar, three-dimensional design such as a swirl pattern 22, to the gelatinous disc 10. The resulting convex face 18 and raised swirl pattern 22 help maintain the eye compress 10 in its position on the eye 12. The mold 20 is preferably of an hourglass shape so as to house two gelatinous discs 16, providing a single therapy session for both eyes 12. The size of the mold 20 is approximately 6.875 inches long by 3.125 inches wide and slightly more than 0.125 inch thick. An open face 24 of the mold 20 is then heat sealed with a clear polyurethane film 26. The clear plastic film 26, which runs over and is adhered to the top of the mold 20, hermetically seals the gelatinous, discs 16 in an air tight, germ free environment while allowing a potential consumer to view the contents of the mold 20 for color preference.

The gelatinous disc-containing and sealed mold 20 is then stored in an anti-static poly aluminum, light impermeable bag 28 to protect the chemical composition and characteristics of the eye compresses 10. The bag 28 includes a resealable zip lock 30 so that a consumer can open the bag 28 to view its contents and reseal the bag 28 if the color or type of eye compresses 10 within the bag 28 are not desired. Also included in the bag 28 is a vial 32 of moisturizer, typically an aloe vera gel, which is utilized when applying the eye compresses 10 as described below. The vial 32 is typically comprised of a 1.5 millilter plastic pillow pack which can be torn open to forcibly excrete the moisturizer contents therefrom. The bag 28 and its contents, particularly the mold 20 containing the eye compresses 10, are stored in a refrigerator to maintain the cool temperature of the gelatinous disc eye compresses 10.

In use, the mold 20 is removed from the refrigerator and the clear plastic film 26 is peeled away from the mold 20. The eye compresses 10 are removed from the specially designed mold 20, and aloe vera based lubricant is removed from the pillow pack 32 and applied to each swirled convex face 18. The aloe vera has beneficial effects on the tissue surrounding the eye and the lubricant helps the eye compress 10 adhere to the eye area after the compress 10 is pressed swirled side down onto the closed eye 12. The eye compresses 10 are preferably allowed to remain on the eye for ten minutes or longer. The healing plant extracts are absorbed into the tissue by osmosis. The aromatherapeutic scents are released from the eye compress 10 to increase its relaxing effect.

Although an embodiment of the invention has been described in detail for purposes of illustration, various modifications may be made without departing from the scope and spirit of the invention. Accordingly, the invention is not to be limited, except as by the appended claims.

What is claimed is:

1. An eye compress, comprising: a molded, gelatinous disk having a convex face configured to overlie a typical human eye and a surrounding margin of tissue, the convex face comprising a non-planar surface, wherein the non-planar surface presents an as-molded, non-uniform, three-dimensional surface for contacting the eye, and wherein the gelatinous disk includes therapeutic plant extracts and oils to relieve and reduce irritation of the eye and surrounding tissue.

2. The eye compress of claim 1, wherein the non-planar surface includes a three dimensional swirl pattern.

3. The eye compress of claim 1, wherein the gelatinous disc comprises a mixture of plant extracts and oils which have therapeutic value, water, gelatin powder, methylparaben, and diazonlidinyl.

4. The eye compress of claim 3, wherein the gelatinous disc comprises a mixture of deionized water, 300 blum gelatin powder, therapuetic plant extracts, peg 40 hydrogenated castor oil, methylparaben, diazolidinyl urea, a coloring agent, and aromatherapeutic oils.

5. The eye compress of claim 1, wherein the gelatinous disc is housed in a hermetically sealed rigid mold which corresponds to the shape of the gelatinous disc.

6. The eye compress of claim 5, wherein the mold includes a plastic film removably covering an open face of the mold so as to hermetically seal the mold.

7. The eye compress of claim 6, wherein the mold containing the gelatinous disc is stored in a light-impermeable and resealable bag.

8. The eye compress of claim 1, wherein the gelatinous disc comprises a cloth-pad free gelatinous disc.

9. The eye compress of claim 1, in which the gelatinous disk is made from ingredients comprising gelatin powder and water.

10. An eye compress, comprising:

a cooled gelatinous disc having a convex face configured to overlie a typical human eye and a surrounding margin of tissue, the convex face including a non-planar, non-uniform and three-dimensional surface for contacting the eye, wherein the gelatinous disc includes water, gelatin powder, methylparaben, diazonlidinyl and therapeutic plant extracts and oils to relieve and reduce irritation of the eye and surrounding tissue, the gelatinous disc being housed in a hermetically sealed rigid mold which corresponds to the shape of the gelatinous disc.

11. The eye compress of claim 10, wherein the non-planar surface includes a swirl pattern.

12. The eye compress of claim 10, wherein the gelatinous disc comprises a mixture of deionized water, 300 blum gelatin powder, therapuetic plant extracts, peg 40 hydrogenated castor oil, methylparaben, diazolidinyl urea, a coloring agent, and aromatherapeutic oils.

13. The eye compress of claim 10, wherein the mold includes a plastic film removably covering an open face of the mold so as to hermetically seal the mold.

14. The eye compress of claim 13, wherein the mold containing the gelatinous disc is stored in a light-impermeable and resealable bag.

15. A method for making and using an eye compress, comprising the steps of:

mixing water, gelatin powder, therapeutic plant extracts, therapeutic oils, methylparaben, and diazonlidinyl to create a gelatinous mixture;

pouring the gelatinous mixture into a mold;

cooling the gelatinous mixture to form a cooled gelatinous disc; and removing the gelatinous disc from the mold and placing the gelatinous disc onto an eye and surrounding tissue to relieve irritation.

16. The method of claim 15, wherein the mixing step includes the step of mixing hot deionized water, gelatin powder, therapeutic plant extracts, hydrogenated castor oil, methylparaben, diazolidinyl urea, a coloring agent, and aromatherapeutic oils.

17. The method of claim 15, wherein the cooling step includes the step of forming the gelatinous mixture into a disc having a convex face with a raised swirl design thereon.

18. The method of claim 17, including the step of applying a moisturizer to the convex face of the gelatinous disc before placing the gelatinous disc on the eye.

19. The method of claim 15, including the step of attaching a plastic film to the mold to hermetically seal the gelatinous disc.

20. The method of claim 19, including the step of storing the gelatinous disc housed in the hermetically sealed mold in a light-impermeable and resealable bag.

21. A method for making and using an eye compress, comprising the steps of:

mixing hot deionized water, gelatin powder, therapeutic plant extracts, hydrogenated castor oil, methylparaben, diazolidinyl urea, a coloring agent, and aromatherapeutic oils to create a gelatinous mixture;

pouring the gelatinous mixture into a mold;

cooling the gelatinous mixture to form a cooled gelatinous disc having a convex face with a raised swirl design thereon;

attaching a plastic film to the mold to hermetically seal the gelatinous disc;

storing the gelatinous disc housed in the hermetically sealed mold in a light-impermeable and resealable bag;

removing the gelatinous disc from the mold;

applying a moisturizer to the convex face of the gelatinous disc; and placing the gelatinous disc onto the eye and surrounding tissue to relieve irritation.

22. A method for making and using an eye compress, comprising the steps of:

forming a mixture comprising water, gelatin powder, therapeutic plant extracts, and therapeutic oils, to create a gelatinous mixture;

pouring the gelatinous mixture into a mold to form a gelatinous disk; removing the gelatinous disk from the mold, and thereafter placing the gelatinous disk onto an eye and surrounding tissue to relieve irritation.

23. The method of claim 22, wherein the gelatinous mixture is molded into a flexible disc having a convex face with a raised swirl design thereon.

24. A method for making and using an eye compress, comprising the steps of:

mixing hot water, gelatin powder, therapeutic plant extracts, and aromatherapeutic oils to create a gelatinous mixture;

pouring the gelatinous mixture into a mold;

cooling the gelatinous mixture to form a cooled gelatinous disk having a convex face with a raised, swirl design thereon;

attaching a plastic film to the mold to hermetically seal the gelatinous disk;

removing the gelatinous disk from the mold;

applying a moisturizer to the convex face of the gelatinous disk; and placing the gelatinous disk onto the eye and surrounding tissue to relieve irritation.

25. The method of claim 24 in which said step of mixing also includes adding hydrogenated castor oil, methylparaben, diazolidinyl urea, and a coloring agent.

26. The method of claim 24 in which said mixing step includes the addition of methylparaben and diazolidinyl urea.

* * * * *

UNITED STATES PATENT AND TRADEMARK OFFICE
CERTIFICATE OF CORRECTION

PATENT NO. : 6,623,517 B1
DATED : September 23, 2003
INVENTOR(S) : DeLuisa et al.

It is certified that error appears in the above-identified patent and that said Letters Patent is hereby corrected as shown below:

Column 3,
Line 59, after "oils", insert -- for direct eye contact --

Signed and Sealed this

Twenty-third Day of December, 2003

JAMES E. ROGAN
*Director of the United States Patent and Trademark Office*